(12) United States Patent
Kostic

(10) Patent No.: US 10,143,608 B2
(45) Date of Patent: Dec. 4, 2018

(54) SYSTEMS AND METHODS FOR DETERMINING THE USABILITY OF PERSON SUPPORT APPARATUSES

(71) Applicant: Stryker Corporation, Kalamazoo, MI (US)

(72) Inventor: Marko N. Kostic, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/709,586

(22) Filed: Sep. 20, 2017

(65) Prior Publication Data

US 2018/0085267 A1 Mar. 29, 2018

Related U.S. Application Data

(60) Provisional application No. 62/398,577, filed on Sep. 23, 2016.

(51) Int. Cl.
*A61G 7/005* (2006.01)
*A61B 5/20* (2006.01)
(Continued)

(52) U.S. Cl.
CPC .............. *A61G 7/005* (2013.01); *A61B 5/202* (2013.01); *A61G 7/05* (2013.01); *A61G 12/001* (2013.01); *F24F 3/1423* (2013.01); *A61F 2013/424* (2013.01); *A61G 7/012* (2013.01); *A61G 2203/30* (2013.01); *B01D 53/14* (2013.01);
(Continued)

(58) Field of Classification Search
None
See application file for complete search history.

(56) References Cited

U.S. PATENT DOCUMENTS 5,299,428 A * 4/1994 Kawaguri ............ A47C 21/044
62/176.6
5,511,006 A 4/1996 Tachibana et al.
(Continued)

FOREIGN PATENT DOCUMENTS

GB 2446870 A 2/2007
JP 2000152964 A 6/2000

OTHER PUBLICATIONS

Nanowire-based Sensors Offer Improved Detection of Volatile Organic Compounds, from NIST Tech Beat, Jun. 21, 2011.
(Continued)

*Primary Examiner* — Curtis J King
(74) *Attorney, Agent, or Firm* — Warner Norcross + Judd LLP

(57) ABSTRACT

A person support apparatus includes a support adapted to support thereon an occupant of the person support apparatus and a sensor configured to detect an ambient air characteristic. The sensor generates an output signal based on the detected characteristic and communicates the output signal to a controller. The controller is configured to receive the output signal from the sensor and determine a usability status of the person support apparatus. The usability status may include an indication that the person support apparatus is ready for use by an occupant, whether a potential hazard exists for an occupant of the person support apparatus, a cleaning status of the person support apparatus, or a location of the person support apparatus.

20 Claims, 8 Drawing Sheets

(51) Int. Cl.
*F24F 3/14* (2006.01)
*A61G 12/00* (2006.01)
*A61G 7/05* (2006.01)
*B01D 53/14* (2006.01)
*G06K 7/10* (2006.01)
*A61F 13/42* (2006.01)
*F24F 110/50* (2018.01)
*F24F 110/66* (2018.01)
*A61G 7/012* (2006.01)

(52) U.S. Cl.
CPC ....... *F24F 2110/50* (2018.01); *F24F 2110/66* (2018.01); *G06K 7/10366* (2013.01)

(56) References Cited

U.S. PATENT DOCUMENTS

| | | | |
|---|---|---|---|
| 5,832,411 | A | 11/1998 | Schatzmann |
| 6,830,581 | B2 | 12/2004 | Magers |
| 7,833,494 | B2 | 11/2010 | MacWhinne et al. |
| 8,597,953 | B2 | 12/2013 | Haick |
| 9,730,847 | B2 * | 8/2017 | Lachenbruch .......... A61G 7/057 |
| 2007/0157385 | A1 * | 7/2007 | Lemire ................. A61G 7/005 5/600 |
| 2007/0243100 | A1 | 10/2007 | Miyauchi et al. |
| 2008/0028533 | A1 * | 2/2008 | Stacy .................... A61G 7/015 5/713 |
| 2011/0085423 | A1 * | 4/2011 | Cottrell ................. G04C 21/02 368/250 |
| 2011/0115635 | A1 * | 5/2011 | Petrovski ............. A47C 21/044 340/584 |
| 2011/0156915 | A1 * | 6/2011 | Brauers .................. A61B 5/02 340/573.4 |
| 2011/0205061 | A1 * | 8/2011 | Wilson ................. G05B 19/042 340/573.1 |
| 2011/0208541 | A1 * | 8/2011 | Wilson .................. A61G 7/018 705/3 |
| 2012/0137436 | A1 * | 6/2012 | Andrienko ............ A61G 7/018 5/600 |
| 2013/0027199 | A1 * | 1/2013 | Bonner ................. G08B 21/24 340/539.11 |
| 2013/0174646 | A1 * | 7/2013 | Martin .................. G01N 33/00 73/31.02 |
| 2014/0276504 | A1 | 9/2014 | Heil et al. |
| 2014/0333440 | A1 * | 11/2014 | Kiani ................... A61B 5/1115 340/573.4 |
| 2015/0257952 | A1 * | 9/2015 | Zerhusen ............. G08C 17/02 340/12.5 |
| 2015/0352313 | A1 * | 12/2015 | Franceschetti ....... A61B 5/4266 600/27 |
| 2016/0015314 | A1 * | 1/2016 | Dusanter ............. A61B 5/4812 600/301 |
| 2016/0015315 | A1 * | 1/2016 | Auphan ............... A61B 5/4815 600/301 |
| 2016/0307429 | A1 * | 10/2016 | Hood .................. G08B 3/1016 |
| 2016/0367420 | A1 | 12/2016 | Zerhusen et al. |
| 2017/0020297 | A1 * | 1/2017 | Luciano ................ A47C 21/003 |
| 2017/0124844 | A1 * | 5/2017 | Huster ................. G08B 21/18 |
| 2017/0245649 | A1 * | 8/2017 | Luciano ................ A47C 21/003 |
| 2018/0049911 | A1 * | 2/2018 | Alzeer ................. A61F 7/0085 |

OTHER PUBLICATIONS

Volatile Organic Compound Discrimination Using Nanostructured Polythiophene Sensors, 2005 IEEE.

* cited by examiner

SYSTEMS AND METHODS FOR DETERMINING THE USABILITY OF PERSON SUPPORT APPARATUSES

CROSS-REFERENCE TO RELATED APPLICATIONS

This application claims priority to U.S. provisional patent application Ser. No. 62/398,577 filed Sep. 23, 2016, by inventor Marko Kostic et al. and entitled SYSTEMS AND METHODS FOR DETERMINING THE USABILITY OF PERSON SUPPORT APPARATUSES, the complete disclosure of which is incorporated herein by reference.

BACKGROUND

The present disclosure relates to systems and methods for determining and communicating the usability status of person support apparatuses, non-limiting examples of which include beds, cots, stretchers, recliners, chairs, operating tables, and the like.

Infection control is a concern in most healthcare facilities. Equipment used with patients must be cleaned and made suitable for use with each patient. The cleaning of person support apparatuses typically involves the use of cleaning solvents. However, some cleaning solvents may leave a residue that could present a problem for certain patients, such as those with respiratory issues or allergies. In some cases, the person support apparatuses are brought to a particular location within the facility for cleaning. However, it can be challenging to monitor and track the usability status of individual person support apparatuses, particularly within a healthcare facility having a multitude of such person support apparatuses.

SUMMARY

In its various embodiments, the present disclosure provides systems and methods to monitor, track, provide feedback and/or train a user regarding a usability status of a person support apparatus.

In one embodiment, a person support apparatus is provided that includes a support adapted to support thereon an occupant of the person support apparatus. A sensor detects an ambient air characteristic and generates an output signal based on the detected characteristic. A controller is configured to receive the output signal from the sensor and determine a usability status of the person support apparatus based on the output signal.

In one aspect, the usability status indicates whether the person support apparatus is ready for use by an occupant. In another aspect, the usability status indicates whether a potential hazard exists for an occupant of the person support apparatus having a compromised health status. The compromised health status may relate to an occupant's respiratory status, allergy status, or other medical status.

In another aspect, the usability status indicates a cleaning status of the person support apparatus. The cleaning status indicates if the person support apparatus has been cleaned or not cleaned. In another aspect, the cleaning status indicates if the person support apparatus has been sufficiently cleaned, insufficiently cleaned, or not cleaned.

In another embodiment, the sensor is adapted to detect volatile organic compounds associated with a cleaning agent used to clean the person support apparatus. The sensor may further be configured to detect at least one additional ambient air characteristic and to use the additional ambient air characteristic to determine the usability status. In one example, the at least one additional ambient air characteristic is a pressure of the air and the controller is adapted to determine a floor of a building on which the person support apparatus is located based upon the pressure of the air. In another aspect, the controller is further adapted to compare a current location of the person support apparatus with a location of a cleaning area within the building to determine if they correspond or not.

In yet another embodiment, the sensor comprises at least two of a volatile organic compound (VOC) sensor, a humidity sensor, an atmospheric pressure sensor, and a temperature sensor. The controller is configured to compare the output signal to reference data stored in a memory accessible by the controller in order to determine the usability status. In some embodiments, the reference data includes a predetermined cleaning profile of the detected characteristic over time. In one example, the predetermined cleaning profile specifies a minimum concentration of volatile organic compounds over a time period, the volatile organic compounds associated with a cleaning agent used to clean the person support apparatus. In another example, the cleaning profile further specifies a predetermined humidity over a time period. In some embodiments, the reference data is communicated to the person support apparatus from an off-board device. The reference data may be configurable by a user of the person support apparatus.

The person support apparatus further includes an indicator, in some embodiments, that is in communication with the controller. The indicator indicates a usability status of the person support apparatus.

In any of the embodiments, the person support apparatus may be one of a bed, a stretcher, a table, a cot, a chair, or the like.

In other embodiments, the person support apparatus further includes a second sensor adapted to detect a second ambient air characteristic and generate a second output signal based on the detected characteristic. The controller determines the usability status based on a combination of the outputs from the two sensors. In other embodiments, the two sensors are each adapted to detect multiple ambient air characteristics and the controller determines the usability status based upon a combination of all of the multiple ambient air characteristics detected by the two sensors.

According to another aspect, a pressure sensor is mounted relative to the support. The pressure sensor detects a contact pressure applied to the support by a person, such as a cleaning person, and generates an output signal based on the detected pressure. The controller uses the output signals from the sensor and the pressure sensor to determine the usability status of the person support apparatus.

According to another embodiment, a person support apparatus is provided that includes a support, first and second sensors, and a controller. The support is adapted to support thereon an occupant of the person support apparatus. The first sensor is adapted to detect a first ambient air characteristic and to generate a first output signal based on the detected first characteristic. The second sensor is adapted to detect a second ambient air characteristic and to generate a second output signal based on the detected second characteristic. The controller determines a usability status of the person support apparatus based on the first output signal and the second output signal.

In one aspect, the first sensor is adapted to detect volatile organic compounds associated with a cleaning agent used to clean the person support apparatus. In another aspect, one of the first or second detected characteristics is a pressure of the air, and the controller uses the detected air pressure to determine a floor of a building on which the person support apparatus is located.

In another embodiment, the first sensor includes a volatile organic compound sensor and the first output signal is indicative of a concentration of volatile organic compounds in the atmosphere adjacent the person support apparatus. The second sensor includes a humidity sensor and the second output signal is indicative of a humidity of the atmosphere adjacent the person support apparatus.

In still another embodiment, the first sensor is configured to detect a first compound (or first class of compounds) and the second sensor is configured to detect a second and different compound, (or second and different class of compounds). The controller determines the usability status based upon reference data indicating a minimum concentration of the first compound (or class of compounds) over time and a minimum concentration of the second compound (or class of compounds) over time.

According to another embodiment, a method of determining a usability status of a person support apparatus is provided. The method includes providing a sensor to detect an ambient air characteristic. The sensor generates an output signal based on the detected characteristic and a usability status of the person support apparatus is determined based on the output signal. The usability status is indicated to a user.

In one aspect, the method includes using the sensor to detect at least one additional ambient air characteristic and to use the additional ambient air characteristic to determine the usability status. In an example, the additional ambient air characteristic is a pressure of the air.

In another embodiment, the method includes using a second sensor to detect a second ambient air characteristic and generate a second output signal based on the detected characteristic. The determination of the usability status is based on a combination of the output signal and the second output signal.

A display is included in some embodiments that is adapted to display an ambient air pressure sensed by an ambient air pressure sensor on board the person support apparatus. In some embodiments, the controller issues an alert if the ambient air pressure passes a threshold. Alternatively, or additionally, the controller uses an output of the ambient air pressure sensor to determine a floor of a building in which the person support apparatus is currently located. In another aspect, the controller monitors the ambient air pressure repetitively and analyzes the repetitive ambient air pressure readings to differentiate weather related changes in ambient air pressure from elevation related changes in ambient air pressure.

Before the various embodiments disclosed herein are explained in detail, it is to be understood that the claims are not to be limited to the details of operation, to the details of construction, or to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
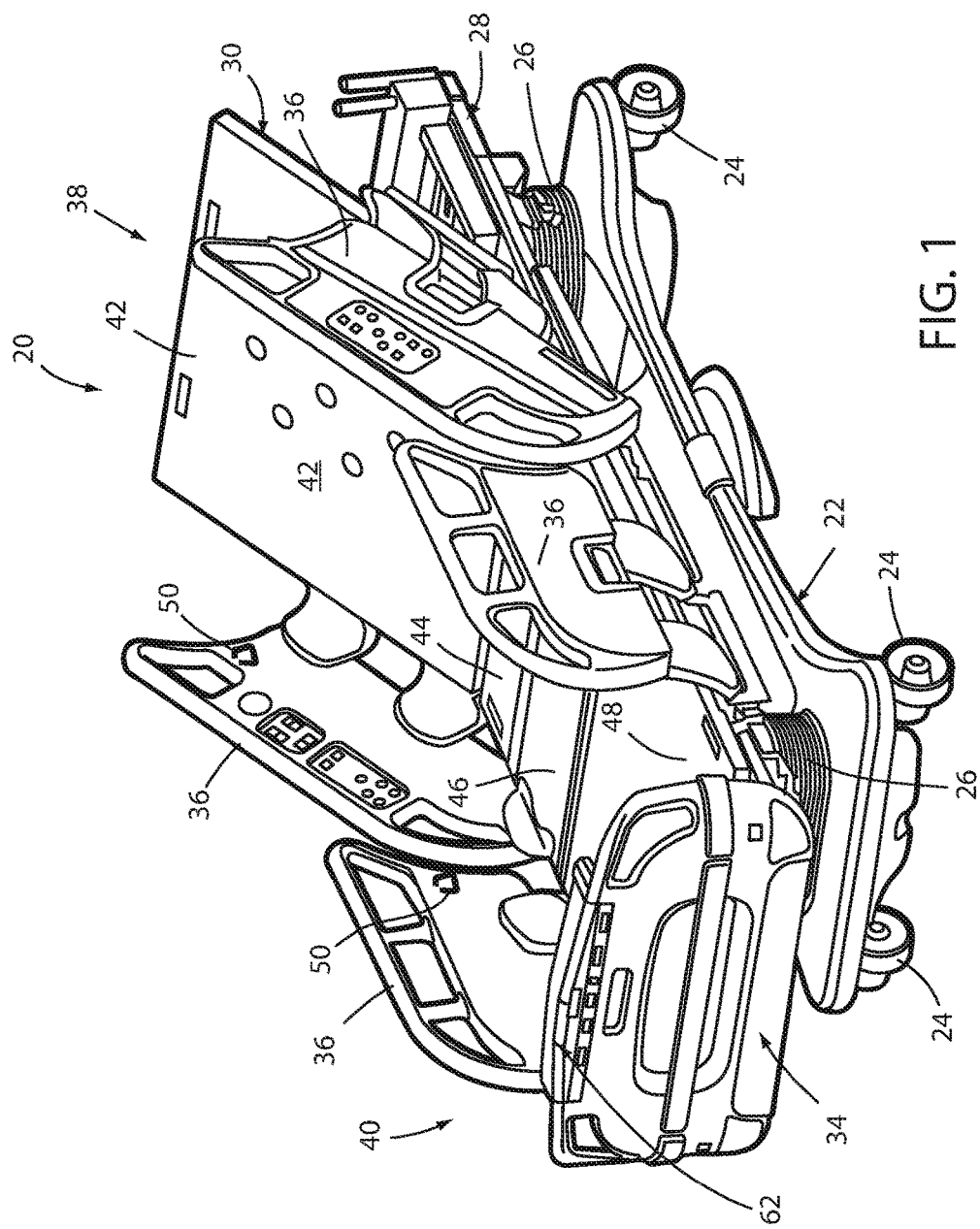
FIG. 1 is a perspective view of one embodiment of a person support apparatus according to one aspect of the present disclosure.

An illustrative person support apparatus 20 that may incorporate one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential. The embodiments herein relate to determining and communicating a usability status of person support apparatus 20. Non-limiting examples of the usability status of person support apparatus 20 include an indication that person support apparatus 20 is ready for use by an occupant, whether a potential hazard exists for an occupant of the person support apparatus 20 having a compromised health status, a cleaning status of person support apparatus 20, and a location of person support apparatus 20 within a building in which person support apparatus 20 is located.

In general, person support apparatus 20 includes a base 22 having a plurality of wheels 24, a pair of lifts 26 supported on the base, a litter frame 28 supported on lifts 26, and a support deck 30 supported on litter frame 28. Person support apparatus 20 further includes a headboard (not shown), a footboard 34, and a plurality of siderails 36. Siderails 36 are all shown in a raised position in FIG. 1 but are each individually movable to a lowered position in which ingress into, and egress out of, person support apparatus 20 is not obstructed by lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Unless indicated otherwise, the mechanical construction of person support apparatus 20 may be the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. Publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Person support apparatus 20 may include an exit detection system (not shown) that is adapted to determine when an occupant, such as, but not limited to, a patient, of person support apparatus 20 is likely to exit person support apparatus 20. Such an exit detection system is adapted to determine when an occupant is likely to leave prior to the occupant actually leaving, and to issue an alert and/or notification to appropriate personnel so that proper steps can be taken in response to the occupant's imminent departure in a timely fashion. The particular structural details of the exit detection system can vary widely. In one embodiment, the exit detection system is constructed and functions in the manner disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference.

Still referring to FIG. 1, person support apparatus 20 also includes one or more sensors 50 mounted to siderails 36 for detecting one or more ambient air characteristics. The exact number and location of sensors 50 can vary. For example, one or more sensors 50 can be mounted to each of the siderails 36 and optionally the headboard and/or footboard 34. Additional sensors 50 may optionally be mounted to support deck 30. Sensors 50 are spaced evenly about a perimeter of support deck 30 or clustered in one or more locations around support deck 30. Each sensor 50 is configured to detect one or more ambient air characteristics. Sensors 50 are mounted to person support apparatus 20 using any suitable mechanical or non-mechanical fastener, non-limiting examples of which include an adhesive, clamps, screws, a snap-fit frame, etc. In some embodiments, sensors 50 are built directly into the components of person support apparatus 20 and are integral therewith.

Figure 2:
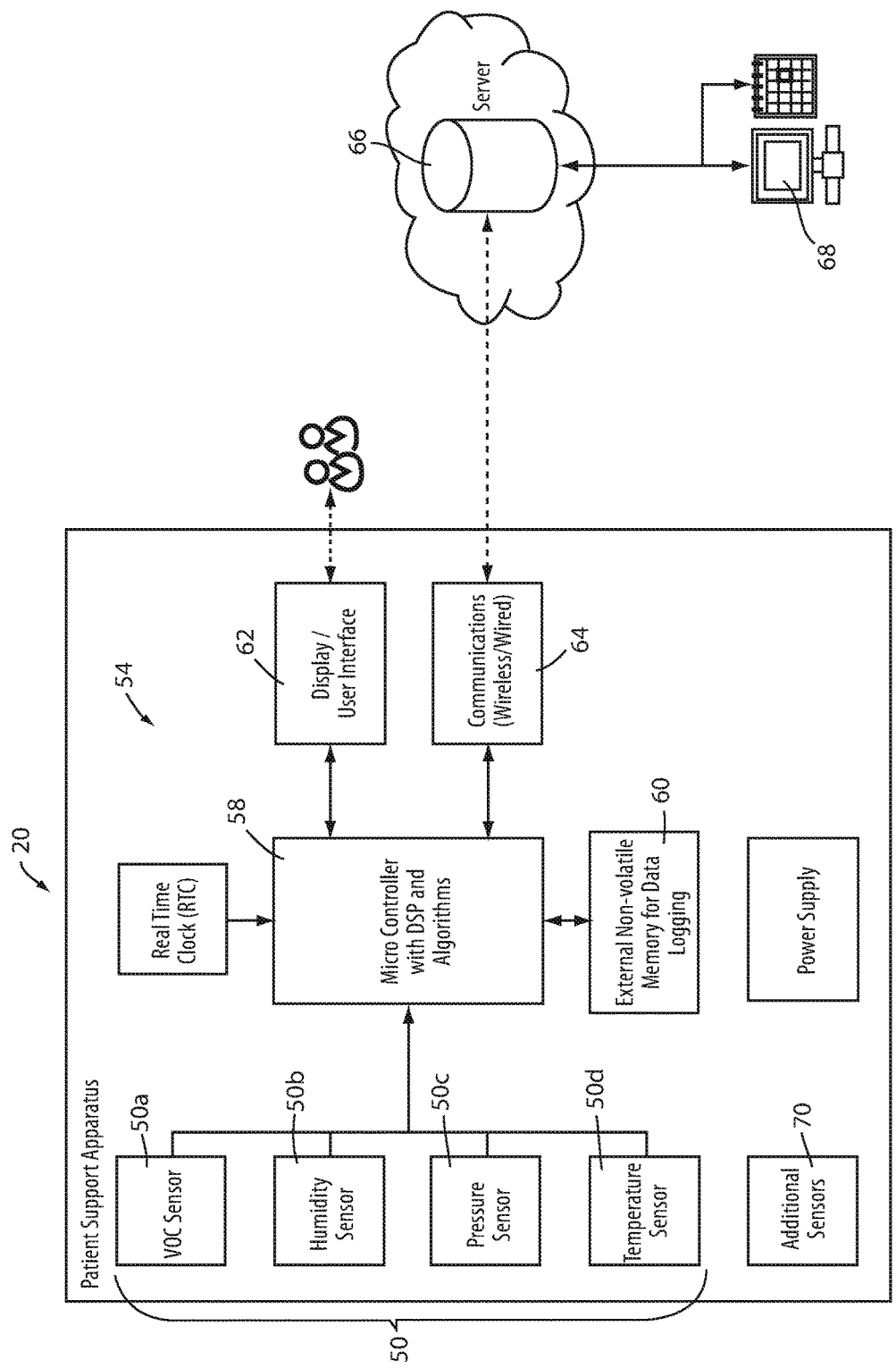
FIG. 2 is a diagram of an embodiment of a control system usable with the person support apparatus of FIG. 1.

Referring now to FIG. 2, person support apparatus 20 includes a control system 54 that is configured to monitor, track, provide feedback and/or train a user regarding a usability status of person support apparatus 20. Control system 54 includes a controller 58 that is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory 60 that is accessible by controller 58.

A user interface 62 communicates with controller 58 and enables a user of person support apparatus 20 to control one or more aspects of person support apparatus 20 and optionally receive information regarding a status of person support apparatus 20. User interface 62 is implemented in the embodiment shown in FIG. 1 as a control panel having a lid (flipped down in FIG. 1) underneath which is positioned a plurality of controls. The controls—which may be buttons, dials, switches, or other devices—allows a user to move the various components of person support apparatus 20, as well as control other aspects of person support apparatus 20. User interface 62 may also include a display for displaying information regarding a usability status of person support apparatus 20. Although FIG. 1 illustrates user interface 62 mounted to footboard 34, it will be understood that user interface 62 can be positioned elsewhere, and/or that one or more additional user interfaces can be added to person support apparatus 20 in different locations, such as siderails 36.

Referring again to FIG. 2, control system 54 includes a transceiver 64 for enabling communication between controller 58 and a network server 66. Transceiver 64 communicates with server 66 through a hard wired connection and/or a wireless connection. In some embodiments, transceiver 64 communicates with network server 66 using Wi-Fi communications, Bluetooth and/or ZigBee communications, or other protocols. Network server 66 is adapted to communicate with a remote interface 68, such as a personal computer, tablet, or smart device. Remote interface 68 may include a display for displaying information regarding a usability status of person support apparatus 20.

Figure 4:
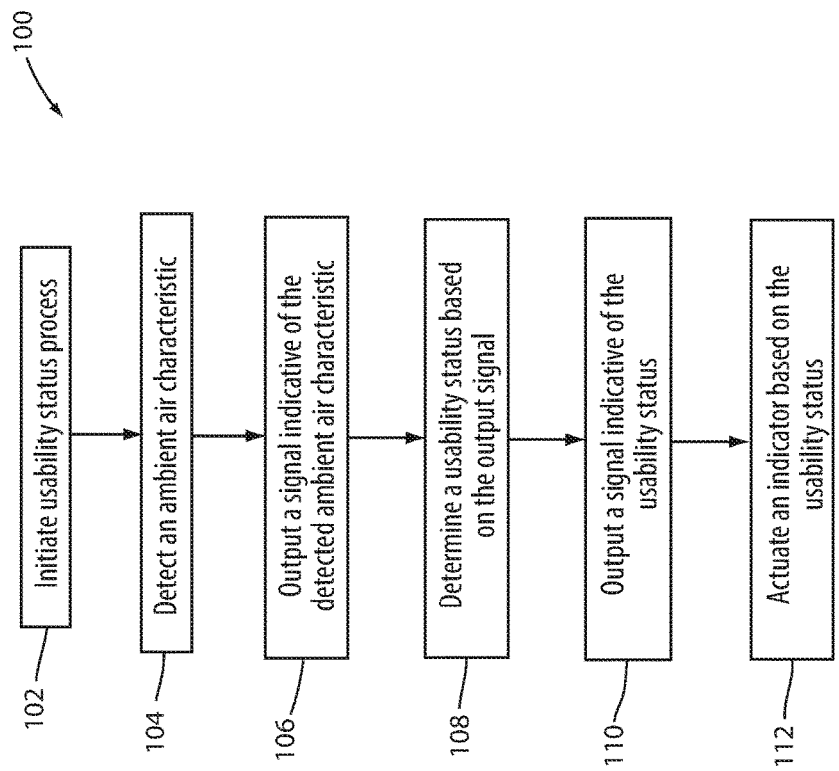
FIG. 4 is a flow chart of an algorithm that may be used by the control system for determining a usability status of the person support apparatus.
Figure 5:
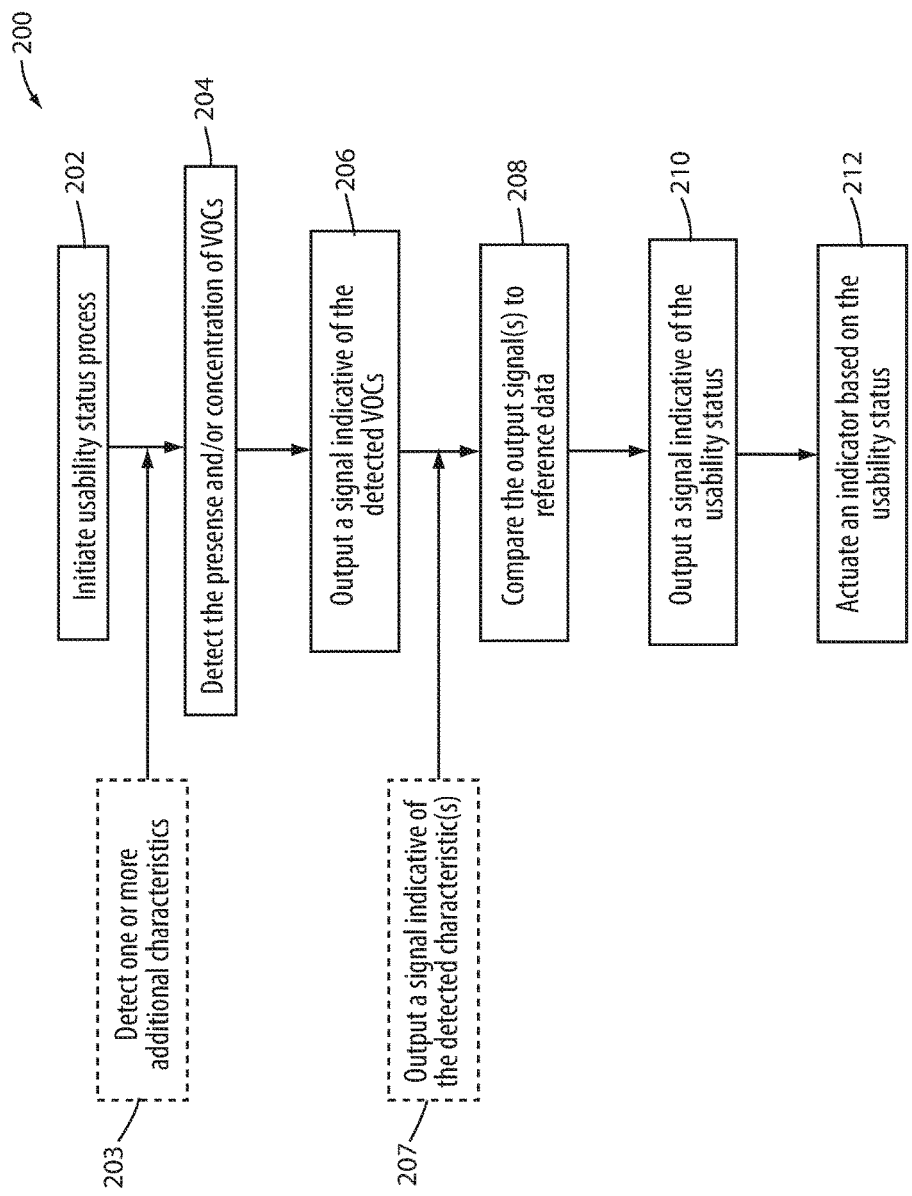
FIG. 5 is a flow chart of an alternative algorithm that may be used by the control system for determining the usability status of the person support apparatus.
Figure 8:
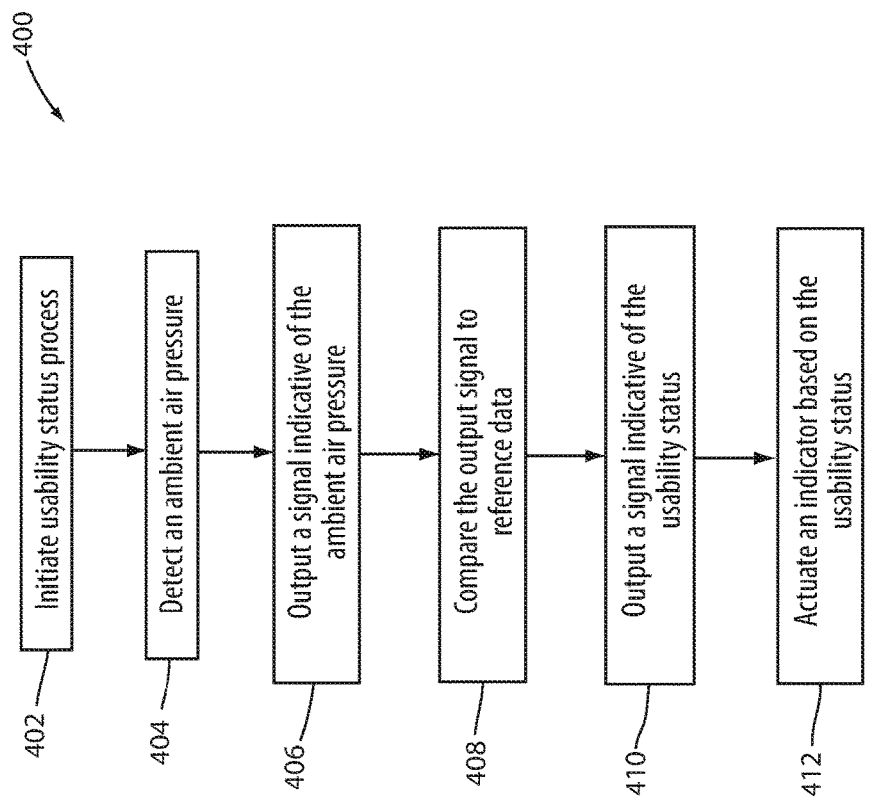
FIG. 8 is a flow chart of yet another algorithm that may be used by the control system for determining the usability status of the person support apparatus.

Control system 54 follows one or more algorithms for determining the usability status of person support apparatus 20. Three of these different algorithms are illustrated in FIGS. 4, 5, and 8. These algorithms monitor, track, provide feedback and/or train a user regarding a usability status of person support apparatus 20. When following the algorithms, control system 54 may stamp information regarding the usability status to create a time log of the date and time regarding the determination of the usability status. The usability status may be based on one or more target thresholds or reference data that varies based on standards and protocols related to the use of person support apparatus 20 and/or based on an occupant using or scheduled to use person support apparatus 20. The standards, protocols, thresholds, and/or reference data are selectable by an appropriate person, such as a healthcare provider, either locally at person support apparatus 20 or at remote interface 68. The standards, protocols, thresholds, and/or reference data are also updatable from time to time when needed or upon request.

Control system 54 is also configured to send notifications regarding the usability status, either through user interface 62 and/or remote interface 68 regarding the usability status. Control system 54 is also configurable to save information, such as login information, usability status determinations, and data from sensors 50 for tracking and/or analysis purposes. In this manner, control system 54 allows a healthcare facility or other provider to analyze, track, and/or monitor information regarding when person support apparatus is ready for use by an occupant, when potential hazards exist for certain occupants, cleaning status (e.g. when and whether person support apparatus 20 was cleaned or not cleaned), and location information related to person support apparatus 20.

User interface 62 and/or remote interface 68 may include controls and displays for one-way and/or two-way communication with a user regarding the usability status of person support apparatus 20. In one example, user interface 62 includes one or more controls (e.g. buttons, switches) or a touch screen that allows a user to initiate a usability status determination process. In another example, user interface 62 includes illuminable status icons, colored lights, and/or a display screen which communicate information regarding the usability of person support apparatus 20 to a user. Optionally, the usability status information is relayed to remote interface 68, which includes illuminable status icons, colored lights, and/or a display screen, in addition to or as an alternative to user interface 62. For example, usability status information indicating that person support apparatus 20 is ready for use or is cleaned or safe for use may be indicated by illuminating a green light or illuminable text or graphics, while a red light or illuminable text or graphics may be used to indicate person support apparatus 20 is not ready for use, has not been cleaned or is not safe for use. In another example, usability status is communicated using audible signals, such as an alarm indicating person support apparatus 20 is not cleaned or not ready for use. Information regarding usability status is determined and displayed in real-time and/or is saved for later analysis and/or display. It will be understood that control system 54 may be configured such that various aspects regarding usability status may be communicated through one or both of user interface 62 and/or remote interface 68 as desired in real-time and/or upon request.

Still referring to FIG. 2, each sensor 50 is a multifunctional sensor having multiple individual sensors 50a-d that detect different ambient air characteristics of the atmosphere adjacent person support apparatus 20. Each sensor 50 can include more than or less than the four individual sensors 50a-d shown in FIG. 2, depending on the intended use. In one embodiment, rather than providing multiple multifunctional sensors 50 on person support apparatus 20, one or more of the individual sensors 50a-d can be mounted to person support apparatus 20. Non-limiting examples of suitable individual sensors include a chemical sensor 50a, a humidity sensor 50b, an ambient air pressure sensor 50c, and a temperature sensor 50d. Chemical sensor 50a is adapted to detect one or more chemicals associated with a cleaning agent used to clean person support apparatus 20, such as volatile organic compounds, a marker chemical, or a fragrance. Humidity sensor 50b, ambient air pressure sensor 50c, and temperature sensors 50d detect the humidity, air pressure, and temperature of the ambient air adjacent to person support apparatus 20. As will be discussed in greater detail below, sensors 50a-d are positioned on person support apparatus 20 at locations where they will be able to detect changes in the ambient air due to the normal evaporation of one or more cleaning agents used to clean person support apparatus 20.

One example of a sensor suitable for use as the sensor 50 is an integrated environmental sensor available from BOSCH Sensortech of Reutlingen, Germany, such as its BME680 integrated sensor. The BME680 sensor is capable of detecting gas, including VOCs, atmospheric pressure, humidity, and temperature. The BMBE680 is a pre-calibrated sensor that is provided with its own software package, which is optionally used with any of the algorithms described herein for determining the usability status. Additional examples of integrated sensors include the BME280 form BOSCH Sensortech, which is capable of detecting pressure, humidity, and temperature. An example of a suitable chemical sensor 50a includes microsensor resistor arrays, such as those described in Li et al., "Volatile Organic Compound Discrimination using Nanostructured Polythiophene Sensors," *IEEE*, p. 191-194, 2005. Another example is a nanowire-based VOC sensor, such as those described in Baum, "Nanowire-based Sensors Offer Improved Detection of Volatile Organic Compounds," *NIST Tech Beat,* 2011 (web). Still other types of sensors may be used.

Optionally, one or more additional sensors 70 are mounted to person support apparatus 20 to provide additional information regarding person support apparatus 20. In one embodiment, sensor 70 is a pressure sensor configured to detect contact pressure applied to one or more surfaces of person support apparatus 20 in the manner disclosed in commonly assigned U.S. Pat. Publication No. 2016/0148485 filed by Hayes et al. and entitled SYSTEM AND METHOD OF MANAGING THE CLEANING OF A MEDICAL APPARATUS, the complete disclosure of which is incorporated herein by reference.

Sensors 50 and 70 are communicably coupled to controller 58 to provide information from sensors 50 and 70 to controller 58 and to optionally receive information from controller 58. Controller 58 is coupled to the sensors 50 and 70 either through a wired or wireless connection. Sensors 50 detect the ambient air characteristics mentioned above (VOC's, pressure, humidity, and temperature) and output signals based on the detected characteristics to controller 58. Controller 58 includes the necessary programming to determine a usability status of person support apparatus 20 based on the output signals received from sensors 50 and optionally sensor 70. In some embodiments, controller 58 communicates the data received from the signals to a controller remote from person support apparatus 20, such as a controller in a personal computer, tablet, or smart device, which includes the software applications to determine a usability status of person support apparatus 20 based on the output signals received from sensors 50 and optionally sensor 70. In other embodiments, controller 58 performs the processing of the outputs from sensors 50 and/or 70 to determine the usability status of person support apparatus 20. Regardless of whether the usability processing is performed locally on person support apparatus 20 or remotely, the usability status of person support apparatus 20 based on output signals received from the sensors 50 (and in some cases sensor 70) is determined, and shared with appropriate personnel.

Figure 3:
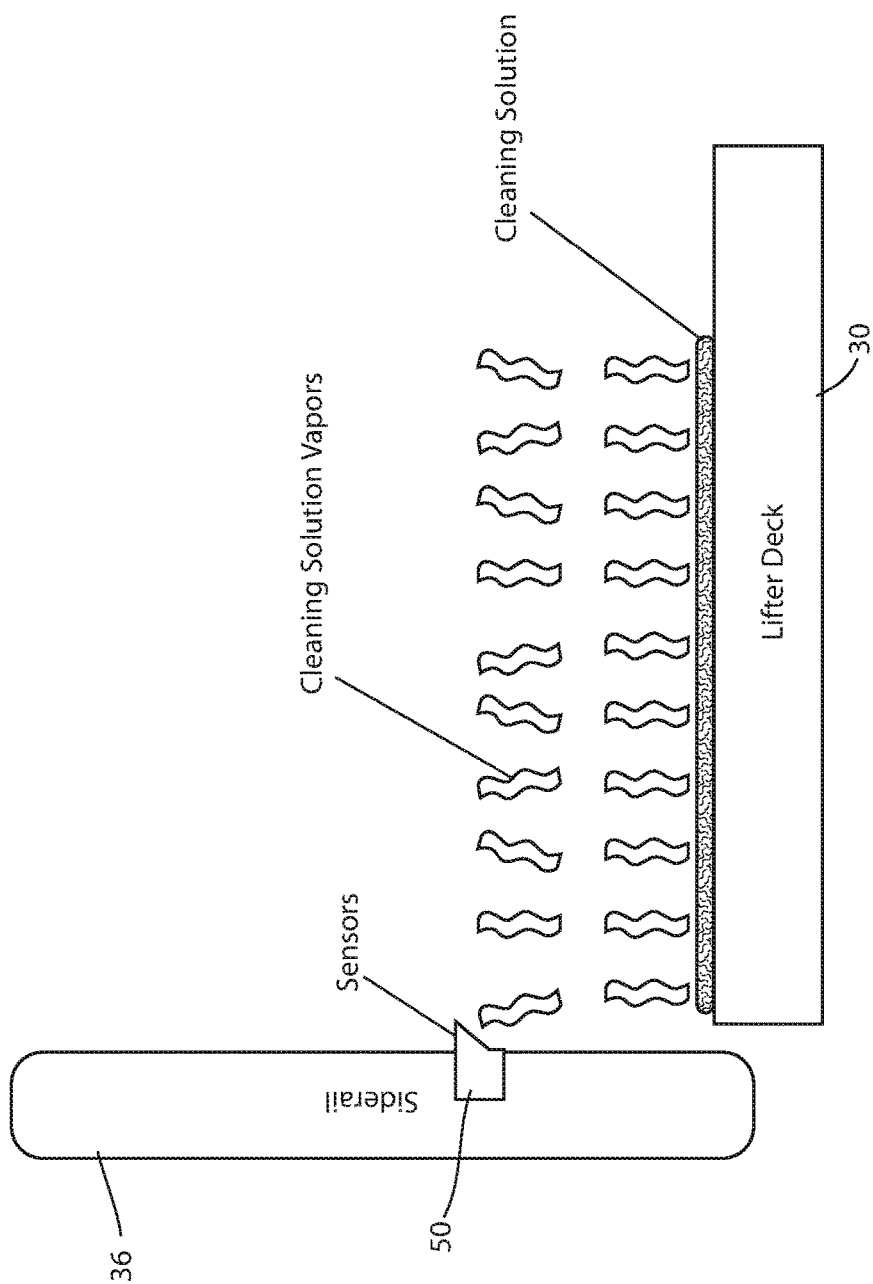
FIG. 3 is a schematic illustration of a portion of the person support apparatus of FIG. 1 showing a sensor detecting volatile organic compounds.

Referring to FIG. 3 sensors 50 are mounted to siderails 36 adjacent support deck 30 such that sensors 50 are capable of detecting air characteristics of the air in the vicinity of support deck 30. During a cleaning process, a cleaning solution is applied by a cleaning person to support deck 30. As the cleaning solution dries, one or more components of the cleaning solution, such as a volatile organic compound, evaporate into the atmosphere adjacent support deck 30 and siderail 36, affecting the characteristics of the ambient air adjacent sensor 50. Sensor 50 detects a presence and/or a concentration of the volatile organic compound in the atmosphere and provides an output signal to controller 58 indicative of the presence and/or concentration of the volatile organic compound. Sensor 50 also detects additional characteristics of the ambient air, such as the humidity, air temperature, and/or air pressure, which are used to provide additional information regarding the cleaning solution used and/or the usability status of person support apparatus 20. As will be discussed more below, controller 58 records the output signals from sensors 50a-d over a time period and uses the recorded values to determine the usability status of person support apparatus 20.

Referring now to FIG. 4, control system 54 executes a usability algorithm 100 depicted therein that determines the usability status of person support apparatus 20. Algorithm 100 may be implemented in software, hardware, or a combination of software and hardware. When implemented with software, algorithm 100 may take on the form of a thin client application, a fat client application, or a local client application. Thin client applications communicate with one or more network services, which are available on one or more remote networks, such as a healthcare facility network and/or the Internet, and the network services perform bulk of the processing. Thick client applications also communicate with one or more network services, but the bulk of the processing is done locally. In some embodiments, controller 58 is configured to support both thick and thin client applications, as well as applications that are purely local.

Algorithm 100 begins with step 102. The commencement of algorithm 100 at step 102 may occur automatically, or it may occur manually in response to a user activating a control on person support apparatus 20, such as a button, icon, switch, lever, etc. It also may commence in response to a user activating a control on a remote device, such as a smart phone, personal computer, nurses' station, etc., that is in communication with person support apparatus 20 via transceiver 64. In one example, algorithm 100 is manually initiated by a user responsible for cleaning person support apparatus 20 just prior to beginning the cleaning process to provide the user with information regarding whether or not the cleaning process has been performed properly and/or whether there are any additional concerns following the cleaning process, such as a potential risk to a future occupant having a compromised health status. When configured to start automatically, algorithm 100 may be running any time person support apparatus 20 has a source of electrical power, or it may commence after one or more of the following events: the exit detection system (if included on person support apparatus 20) detects that there is no occupant of person support apparatus 20; the patient assigned to person support apparatus 20 is discharged from the corresponding medical facility; a message is sent from a network service or application via transceiver 64; data stored regarding a particular patient assigned to person support apparatus 20 is deleted from the memory of person support apparatus 20 via user interface 62; and/or other events.

After usability algorithm 100 is initiated, ambient air characteristic sensors 50a-d, and optionally pressure sensor 70, are activated at step 104 to begin collecting information regarding one or more ambient air characteristics. With respect to the embodiment of FIG. 2, this includes chemical sensor 50a detecting a presence and/or a concentration of one or more volatile organic compounds (or classes of compounds), humidity sensor 50b detecting a humidity of the atmosphere, ambient air pressure sensor 50c detecting the atmospheric pressure, and temperature sensor 50d detecting the air or surface temperature. In another example, person support apparatus 20 includes only one type of sensor, such as VOC compound sensor 50a, or a sub-combination of sensors, such as chemical sensor 50a and humidity sensor 50b. One or more of the sensors 50a-d, controller 58, or both include a clock for measuring one or more of the ambient air characteristics over time.

At step 106, sensors 50a-d output a signal indicative of the corresponding ambient air characteristic to controller 58. The sampling time and sampling rate of sensors 50a-d is set based on the characteristics of each sensor 50a-d and the data needed for determining the usability status from the output signals. Controller 58 utilizes the output signals received from sensors 50a-d at 108 to determine the usability status of person support apparatus 20. In one embodiment, algorithm 100 compares the output signals received from one or more of sensors 50a-d with reference data stored in memory 60. The format of the reference data is based on the type of information provided by sensor 50a-d. In one example, the reference data is in the form of a predetermined cleaning profile of the detected characteristic, such as the concentration of volatile organic compounds over a predetermined period of time or the concentration of volatile organic compounds compared to the measured humidity. In another example, the reference data is in the form of a data look-up table including predetermined ambient air characteristics or ranges of ambient air characteristics that correspond to a particular outcome. In some embodiments, a data look-up table is used to compare the ambient air pressure detected by sensor 50c with air pressure data corresponding to a particular floor in a building in which person support apparatus 20 is located.

In some embodiments, one or more components of the reference data are stored in a memory of an off-board device that is communicatively coupled to controller 58, such as through server 66, rather than in memory 60 on board person support apparatus 20. The reference data is pre-programmed but configurable by a user. Changing of the reference data is carried out via user interface 62 and/or via remote interface

68. In some embodiments, controller 58 communicates the sensor signals to a remove device, (e.g. a computer associated with remote interface 68) which compares the sensor signals to the reference data, determines usability status of person support apparatus 20, and then communicates the usability status back to person support apparatus 20.

The usability status of person support apparatus 20 may refer to the cleaning status and/or the air quality status of person support apparatus 20. When referring to the cleaning status, the usability status may refer to any one or more of the following: whether person support apparatus 20 has been cleaned or not; whether person support apparatus 20 has been sufficiently cleaned or insufficiently cleaned; and whether person support apparatus 20 is in the process of being cleaned (e.g. a cleaning agent has been applied, but insufficient time has passed for proper disinfection to have occurred). when referring to the air quality status, the usability status refers to whether a potential health hazard exists for an occupant of person support apparatus 20 having a compromised health status (e.g. asthma, allergies, etc.), or whether a potential health hazard exits for an occupant who does not have a compromised health status. The usability status—both cleaning related and air quality related—is determined at step 108 of algorithm 100. However, in some embodiments, algorithm 100 is modified to only determine one status, such as cleaning or air quality, and not both.

In general, the cleaning status is determined by comparing the amount or concentration of detected volatile organic compounds to a threshold level (included within the above-mentioned reference data) and determining whether the threshold has been exceeded for a minimum amount of time. The detected VOC corresponds to one or more VOCs that are associated with the cleaning agents commonly used to clean person support apparatus 20, and/or one or more cleaning agents that are specifically used at the healthcare facility in which person support apparatus 20 is located. Further discussion of how this cleaning status is determined is provided below with respect to the description of FIG. 6.

In general, the air quality status if determined by comparing the current amount of VOCs detected to one or more thresholds that are part of the above-mentioned reference data. The thresholds are associated with VOC levels that may cause discomfort to a person having a compromised health status and/or VOC levels that are known or believed to be harmful to such individuals. The air quality status determination at step 108 may also compare the currently detected VOC levels to thresholds that correspond to individuals who do not have a compromised health status. Further discussion of how the air quality status of person support apparatus 20 is determined is provided below with respect to FIG. 7.

As used herein, the term "cleaning" encompasses any one of more of the following: removing, degrading, and/or otherwise breaking down unwanted matter on surfaces of person support apparatus 20, treating surfaces of person support apparatus 20 by the application of one or more cleaning agents, and/or disinfecting surfaces of person support apparatus 20. The term disinfecting is used herein to encompass killing, destroying, inhibiting growth and reproduction, and/or otherwise rendering innocuous biological organisms, such as bacteria, protists, fungus and mites, for example, and/or infectious agents, such viruses and prions. It is understood that a degree or level of disinfecting is based on several factors, non-limiting examples of which include a type of cleaning agent used and a time of treatment with a cleaning agent.

At step 110, controller 58 outputs a signal indicative of the usability status (cleaning status, air quality status, and/or both) of person support apparatus 20. That signal, as indicated by step 112, updates and/or changes an indicator regarding the usability status of person support apparatus 20. In one example, the output signal activates a light and/or generates a sound coming from user interface 62. In another example, the output signal illuminates one or more status icons, colored lights, and/or a display screen on user interface 62. In still another example, the output signal is transmitted via transceiver 64 to remote interface 68, which updates and/or changes information displayable thereon regarding the usability status of person support apparatus 20. As noted, remote interface 68 may be a nurse call station or a healthcare facility network or some other type of infrastructure that provides alerts to personnel interested in the status of person support apparatus 20. Information regarding the usability status of person support apparatus 20 may be displayed locally or remotely in a real-time to a user. In some embodiments, the usability status is forwarded by algorithm 100 to a network service that stores the data to allow logging of and/or analysis of the data. In one example, the usability status information is stored and accessed when needed to determine the usability status of a particular person support apparatus 20 prior to use by an occupant.

When indicating the usability status of person support apparatus 20 at step 112, some embodiments of person support apparatus 20 include multiple indicators that are used for indicating different aspects of person support apparatus 20. For example, a first indicator may indicate the cleaning status of person support apparatus 20 while a second indicator may indicate the air quality status of person support apparatus 20. In such situations, person support apparatus 20 may report different usability statuses of person support apparatus 20 at different times. For example, when a cleaning agent is first applied to person support apparatus 20, controller 58 may determine the VOX levels are too high for someone with compromised health, and therefore active an indicator that indicates the person support apparatus 20 is not currently safe for use with certain individuals. At the same time, the VOC levels may not have been detected for a long enough time period to satisfy the cleaning standards, so controller 58 may active another indicator that indicates that person support apparatus 20 has not been cleaned. When the cleaning is finished, controller 58 may change this indicator to indicate that person support apparatus 20 is cleaned. However, the indicator of undesired air quality for certain individuals may still be activated, depending upon the VOC levels, and may continue to be activated for as long as it takes for those VOC levels to dissipate.

In some embodiments, person support apparatus 20 includes a "last cleaned on" identifier that is display on user interface 62. In such embodiments, controller 58 automatically updates this indicator when it detects VOC levels associated with a cleaner that are of sufficiently high concentration for a predetermined time period so as to indicate that person support apparatus 20 has been cleaned, as will be discussed more below. In some of such embodiments, controller 58 does not provide a "dirty" or "not cleaned" indication, but instead may simply include the date of last cleaning, while in others of such embodiments, controller 58 provides both the date of last cleaning and the current cleaning status.

Referring now to FIG. 5, an alternative exemplary algorithm 200 for determining a usability status based on outputs from chemical sensor 50a is illustrated. In this example, chemical sensor 50a detects and outputs a signal indicative of a concentration and/or presence of a group of VOCs or a particular VOC. Following initiation of algorithm 200 at step 202 (which is initiated in any of the same manners discussed above with respect to the initiation of algorithm 100), chemical sensor 50*a* is activated to begin detecting the presence and/or the concentration of VOCs in the ambient air at 204. The VOCs are associated with one or more cleaning agents used to clean person support apparatus 20. Chemical sensor 50*a* therefore detects a presence of at least one VOC in the ambient air that is associated with the cleaning agents being used. Alternatively or additionally, chemical sensor 50*a* detects a concentration of total VOCs or a particular VOC associated with the cleaning agents being used. In one example, multiple VOC sensors 50*a* are used that each detect a particular VOC that is associated with the cleaning agents being used.

At step 206, chemical sensor 50*a* outputs a signal indicative of the detected VOCs in the ambient air. The output signal is indicative of either the presence or a concentration of the detected VOCs. Chemical sensor 50*a* optionally includes a clock that allows chemical sensor 50*a* to output a signal of the detected presence or concentration of VOCs over time or controller 58 includes a clock for recording the incoming output signal from chemical sensor 50*a* over time.

The output signal indicative of the detected VOCs is compared at step 208 with reference stored in memory 60 of controller 58. Alternatively, the output signal is communicated to server 66 for comparison with reference data stored in a memory accessible to server 66. In one embodiment, the reference data includes a predetermined cleaning profile that specifies a minimum concentration of the detected VOCs over a time period.

Figure 6:
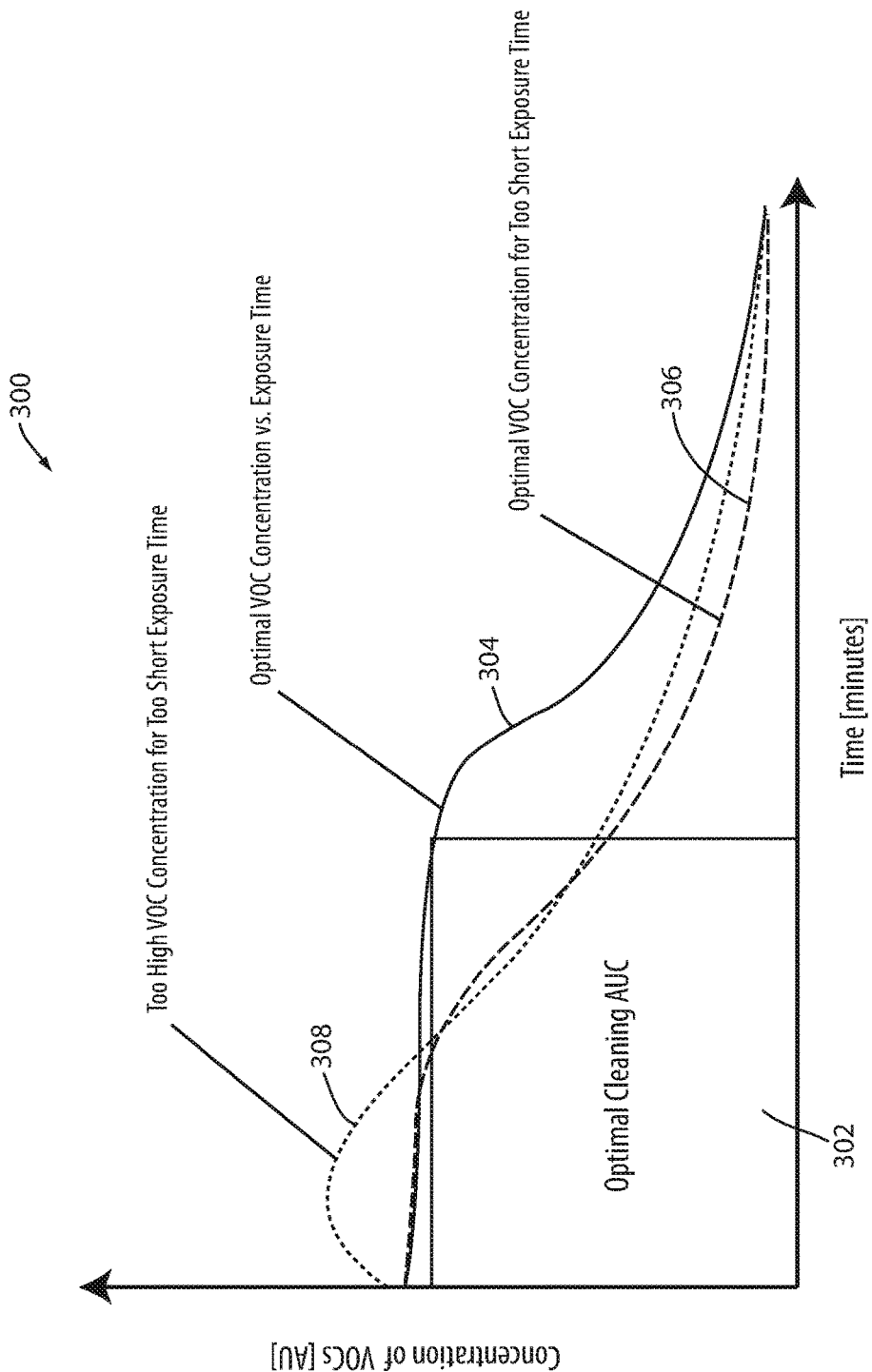
FIG. 6 is a graph of an illustrative cleaning profile that may be used by the control system for determining the usability status of the person support apparatus.

An exemplary cleaning profile 300 is illustrated in FIG. 6 for use by algorithms 100 and/or 200 as the reference data for comparison with the output signal at steps 108 and/or 208. The cleaning profile 300 includes a predetermined minimum concentration of VOCs over a time period that corresponds to a particular usability status, such as a cleaned status, which is illustrated by zone 302. Both VOC concentration and time at that VOC concentration affect the degree to which the surface is cleaned. The minimum concentration and time period corresponding to a cleaned status is determined based on empirical data or other cleaning standards. The empirical data or other standard data corresponds to treatments at given concentrations of VOCs that yield desired degrees of cleaning. Different data may be used for different cleaning agents or solutions.

Controller 58 receives the output signal from chemical sensor 50*a* indicative of a concentration of VOCs and compares the concentration to the zone 302. If the concentration of VOCs is at or above the concentration defined by zone 302 for the length of time defined by zone 302, as illustrated by curve 304, controller 58 outputs a signal at 210 indicating a cleaned or satisfactorily cleaned status. If the concentration of VOCs satisfies the concentration defined by zone 302, but does not stay above that concentration for the length of time defined by zone 302, as illustrated by curve 306, controller 58 outputs a signal at 210 indicating an uncleaned or unsatisfactorily cleaned status. In such situations, controller 58 may be programmed to send a message to the cleaner, or the cleaning department, indicating that the person support apparatus 20 should be re-cleaned.

Curve 308 illustrates a scenario in which a high concentration of VOCs is detected from the cleaning agent used to treat person support apparatus 20, but that high concentration is not maintained for long enough to satisfactorily clean the surface. That is, if the concentration of VOCs satisfies the desired minimum concentration defined by zone 302, but the concentration is not maintained for the length of time defined by zone 302, as illustrated by curve 308, controller 58 outputs a signal at step 210 indicating an uncleaned or unsatisfactorily cleaned status.

Controller 58 may also analyze the detected concentration of VOCs to determine if person support apparatus 20 is safe for use by an occupant, and optionally, whether person support apparatus 20 is safe for use by an occupant having a compromised health status. If the concentration of VOCs indicated by curve 308 is higher than an air quality reference threshold, controller 58 outputs a signal at step 210 indicating that person support apparatus 20 is not safe for use by an occupant, or specifically that person support apparatus is not safe for an occupant having a compromised health status. In one example, the VOC concentration threshold corresponds to a threshold that is deemed hazardous or potentially hazardous for any occupant. Additionally, or alternatively, the VOC concentration threshold corresponds to a threshold that is deemed hazardous or potentially hazardous for an occupant having a compromised health status. For example, the VOC concentration threshold for an occupant having respiratory challenges or an allergy to certain cleaning agents is lower than the VOC concentration threshold for an occupant without such health issues.

When detecting the air quality status of person support apparatus 20, controller 58 automatically repeats the detection and analysis steps (e.g. steps 104-110, 204-210) so that when the detected VOC concentrations have dissipated to below the threshold air quality thresholds, controller 58 will detect this. In response to detecting that the air quality has improved to the level of being safe for an occupant, controller 58 proceeds to step 212 (or step 112 for algorithm 100) and updates a status indicator regarding the air quality status of person support apparatus 20. In this manner, potential users of person support apparatus 20 are automatically notified when the VOC levels associated with person support apparatus 20 have dissipated sufficiently to meet the corresponding air quality standard. As noted previously, the air quality standards can be configured by authorized personnel so that healthcare facilities can customize the standards to their own preferences.

The output signal generated at step 210 activates a visual and/or audible indicator at step 212. The activation of the indicator(s) may occur in any of the same manners discussed above with respect to step 112 of algorithm 100. Non-limiting examples of the types of indicators include illuminable status icons, colored lights, and/or a display screen on user interface 62 and/or remote interface 68, the latter of which receives information regarding the usability status of person support apparatus 20 from controller 58. In one example, the cleaning indicator is a colored light or colored icon on a display, such as red, green, and yellow, that communicates to a user that person support apparatus 20 is not cleaned (red indicator lit), cleaned or sufficiently cleaned (green indicator lit), or is insufficiently cleaned or cleaning needs to be extended/repeated (yellow indicator lit). In another example, an air quality status indicator includes an alarm that is sounded and/or a status icon that is illuminated and that indicates that person support apparatus 20 may be hazardous for occupants in general and/or hazardous for specific occupants with a compromised health status. When an audible signal is used, it may be used alone or in combination with a visual indicator to communicate the usability status of person support apparatus 20. In one example, the output signal generated at 210 is stored by server 66 for later review and/or analysis.

In some embodiments, algorithm 200 utilizes information from multiple groups of chemical sensors 50a that are configured to detect the concentration of different chemicals over time. For example, a first group of chemical sensors 50a outputs a signal indicative of the concentration of a first VOC (or first class of VOCs) over time and a second group of chemical sensors 50a outputs a signal indicative of the concentration of a second VOC (or second class of VOCs) over time. At step 208, controller 58 compares the output signals from both the first and second group of chemical sensors 50a to reference data relevant to the respective first and second VOCs. Controller 58 determines the usability status based on the comparison with the reference data for both the first and second group of chemical sensors 50a. The reference data indicates a minimum concentration of each of the first and second VOCs over a predetermined period of time. If the comparison indicates that one or both of the first and second VOCs does not satisfy the minimum concentration for the predetermined period of time, controller 58 outputs a signal indicating that person support apparatus 20 is not cleaned or is not sufficiently cleaned. If the comparison indicates that the concentration of both the first and second VOCs satisfies the corresponding minimum concentration for the predetermined period of time, controller 58 outputs a signal indicating that person support apparatus 20 is cleaned or sufficiently cleaned.

In one example, the first VOC is present in a first cleaning agent that is used in a first cleaning stage and the second VOC is present in a second cleaning agent that is used in a second cleaning stage. Controller 58 uses the presence of both the first and second VOCs to determine that both the first and second cleaning stages were performed according to protocol. In another example, the first and second VOCs are present in the same cleaning agent. When present in the same cleaning agent, the first and second VOCs may have different dissipation rates that are used by controller 58 to determine that the cleaning agent was applied in both the correct concentration and for the correct amount of time. Alternatively, the first and second VOCs may be present in the same cleaning agent and, regardless of their dissipation rates, controller 58 uses the presence of both VOCs to distinguish the desired cleaning agent from other cleaning agents that may have only one or none of the VOCs. In other words, the two different VOCs that are detected are chosen as being indicative of a specific cleaning agent or class of cleaning agents that excludes one or more undesired or unapproved cleaning agents. By adding even more chemical sensors 50a, confirmation of the use of a specific cleaning agent can be detected with greater reliability. Chemicals other than VOCs, such as a marker chemical, are usable in a similar manner in order to detect a specific chemical signature of the desired cleaning agent.

In some embodiments, algorithm 200 utilizes output from additional sensors, such as humidity sensor 50b, in addition to chemical sensor 50a in determining a usability status of person support apparatus 20. This information may be used alone or in combination with cleaning profile 300 to determine the usability status. In one embodiment, humidity data from humidity sensor 50b is used to provide information regarding the cleaning status and/or the air quality of person support apparatus 20. Algorithm 200 includes an additional step 203 of detecting the humidity adjacent person support apparatus 20 and outputting a signal indicative of the humidity at step 207. Controller 58 receives the output signals from chemical sensor 50a and humidity sensor 50b indicative of the VOC concentration and humidity, respectively, over time. The output signals are compared at step 208 with reference data for determining a usability status. The reference data includes a range or threshold of VOC concentration compared to humidity that is indicative of a usability status. At step 210 controller 58 outputs the results from its comparison of the VOC and humidity levels. At step 212, one or more usability status indicators are updated and/or changed based on the signals output at step 210.

Figure 7:
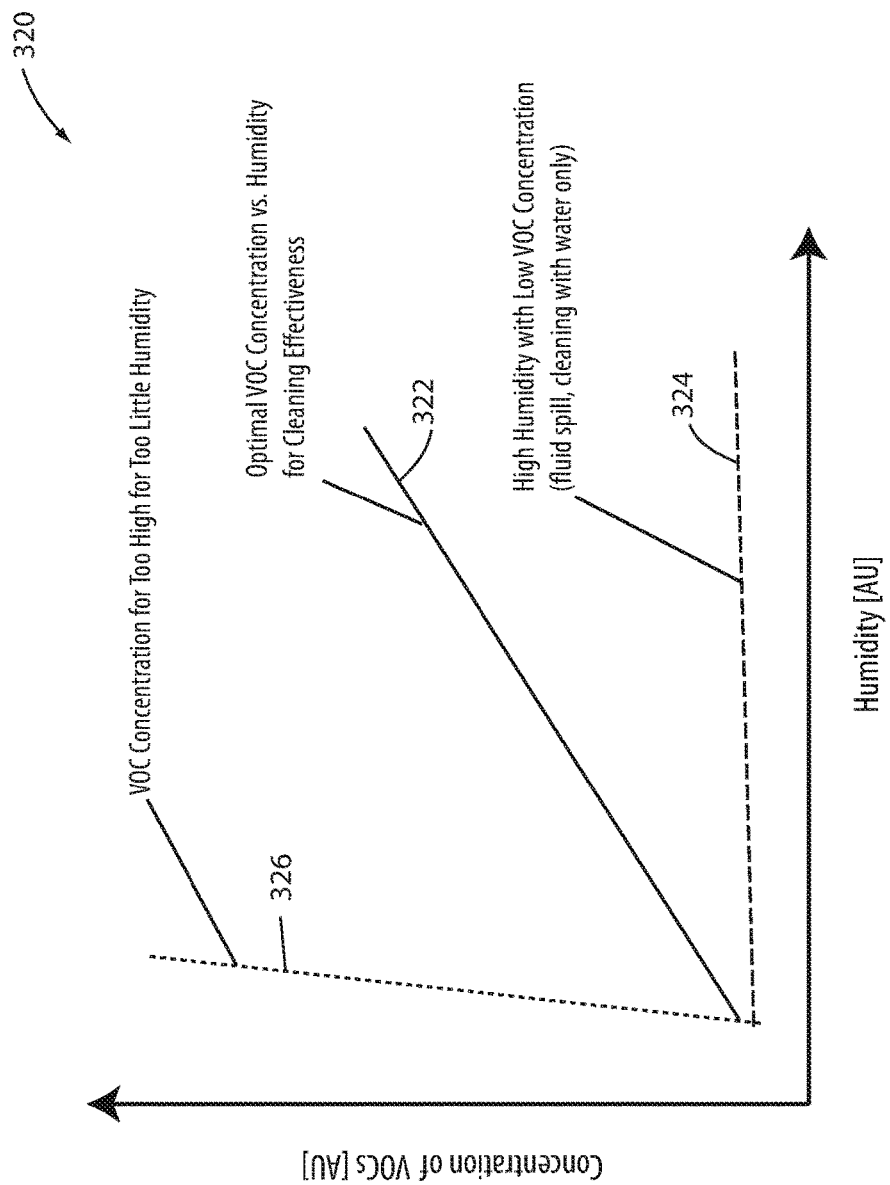
FIG. 7 is a graph of another illustrative cleaning profile that may be used by the control system for determining the usability status of the person support apparatus.

Referring now to FIG. 7, graph 320 illustrates three example scenarios determined using output signals from chemical sensor 50a and humidity sensor 50b. At step 208, controller 58 compares the VOC and humidity sensor output signals with the reference data. If the VOC and humidity sensor output signals satisfy a predetermined threshold, as illustrated by curve 322, controller 58 generates an output signal at 210 indicating that the surface has been cleaned or sufficiently cleaned. If the VOC and humidity output signals are below the predetermined threshold, as illustrated by curve 324, controller 58 generates an output signal at 210 indicating that the surface has not been cleaned or sufficiently cleaned. For example, if the VOC concentration is too low, cleaning may not have occurred to the desired degree. In addition, some amount of water is required to destroy certain bacteria, and thus a low humidity may suggest that not enough water was used to destroy water-sensitive bacteria. Curve 324 is illustrative of a scenario in which water was spilled or used alone for cleaning, or a scenario in which the VOC-containing solution was diluted with too much water. A low VOC concentration or undetected VOC concentration is also indicative of scenarios in which the wrong cleaning solution was used, such as a bleach or soap solution being used.

If the VOC and humidity sensor output signals are above the predetermined threshold or range, such as illustrated by curve 326 (FIG. 7), controller 58 generates an output signal at step 210 indicating that the surface has not been cleaned or sufficiently cleaned. Curve 326 is illustrative of a scenario in which the VOC-containing cleaning solution was not diluted enough or not rinsed with enough water, as demonstrated by the low humidity readings. Such a scenario is indicative of the surface not being properly cleaned and/or indicative of a scenario in which person support apparatus 20 is not ready for use by an occupant. A high concentration of VOCs and low humidity may be an indicator of an air quality status that could be of concern for occupant's having a compromised health status, such as a compromised respiratory status or a compromised allergy status. Thus, in one embodiment, if controller 58 determines the VOC and humidity output signals are above a predetermined VOC vs humidity threshold or range, controller 58 generates an output signal at 210 indicative of person support apparatus 20 not being ready for use and/or being a potential hazard for an occupant having a compromised health status.

In another example, in addition to detecting VOCs, chemical sensor 50a detects other chemical compounds present in the air adjacent person support apparatus 20. Algorithm 200 is then used in the same manner as described above regarding VOCs to determine the usability status of person support apparatus 20 based on the presence and/or concentration of the particular chemical compounds detected by chemical sensor 50a. In one example, the cleaning agent used to clean person support apparatus 20 includes a marker chemical that is detectable by the chemical sensor 50a. The marker chemical is a chemical that is added to the cleaning agent to identify the cleaning agent. In another example, the chemical sensor 50a is configured to detect a fragrance present in the cleaning agent used to identify the cleaning agent. In one embodiment, a change in concentration or presence of the marker chemical or fragrance over time is used to determine the cleaning status of person support apparatus 20 in a manner similar to what is described above for algorithm 200 with respect to FIG. 6. In another embodiment, a change in concentration or presence of the marker chemical or fragrance over time compared to the detected humidity is used to determine the cleaning status of person support apparatus 20 in a manner similar to what is described above for algorithm 200 with respect to FIG. 7. In still another example, the marker chemical or fragrance is used to determine that a particular cleaning agent was used.

In still another embodiment, a first group of chemical sensors 50a is adapted to detect VOCs and a second group of chemical sensors 50a is adapted to detect one or more particular chemical compounds, such as a marker chemical. The signal output from the first group of chemical sensors 50a regarding the VOC concentration is used in the same manner as described above in algorithm 200 to determine the usability status of person support apparatus 20. In this embodiment, algorithm 200 includes an additional step between steps 208 and 210 in which the output signal from the second group of chemical sensors 50a is used by controller 58 to determine that the correct cleaning agent was used based on the presence of a predetermined marker chemical detected by the second group of chemical sensors 50a. The output signals from both the first and second group of chemical sensors 50a are used at step 210 to determine the usability status. In this manner algorithm 200 uses the chemical sensors 50a, and optionally humidity sensor 50b, to determine that person support apparatus 20 was cleaned to a predetermined degree but also using a predetermined chemical agent.

In another example, algorithm 200 uses information from temperature sensor 50d at 207 to determine the usability status. Certain combinations of cleaning chemicals may react endothermically, reducing the air and/or surface temperature, or exothermically, increasing the air and/or surface temperature. The air and/or surface temperature may also decrease during evaporation of a solvent of the cleaning solution used to clean person support apparatus 20, such as an alcohol solvent. In one example, temperature sensor 50d is an air temperature sensor and changes in the air temperature are used at 208 to determine if the correct cleaning solution was used. In another example, temperature sensor 50d is a non-contact temperature sensor, such as an infrared temperature sensor, and changes in the surface temperature are used at 208 to determine if the correct cleaning solution was used. Controller 58 includes reference data corresponding to threshold temperature data or rate of temperature change that is compared to the detected temperature at 208 to determine if the correct cleaning solution was used. This information is used alone or in combination with the chemical sensor information to determine the usability status of person support apparatus 20, as described above.

In some embodiments, information from chemical sensor 50a, humidity sensor 50b, and temperature sensor 50d, is used to provide a cleaning solution profile or "fingerprint". Controller 58 includes stored cleaning solution fingerprints for comparison with the detected characteristics. If the detected fingerprint matches one of the stored, acceptable fingerprints, the output signal at 210 indicates that the correct cleaning solution was used and a corresponding indicator is activated at 212. If the detected fingerprint does not match one of the stored, acceptable fingerprints, the output signal at 210 indicates that the correct cleaning solution was not used and a corresponding indicator is activated at 212. In one example, the acceptable cleaning solution corresponds to a prospective occupant of person support apparatus 20. If the prospective occupant has a compromised health status, such as respiratory challenges, controller 58 uses the cleaning solution fingerprint to determine whether the cleaning solution used to clean person support apparatus 20 is safe for an occupant with respiratory challenges. Different cleaning protocols may be associated with different cleaning solutions based on the previous use of persons support apparatus 20 and/or the future use of person support apparatus 20. The cleaning solution fingerprint is used by controller 58 to determine if the correct cleaning solution was used based on the particular cleaning protocol.

In another embodiment, information from temperature sensor 50d is used to calibrate the data from the chemical sensor 50a and/or humidity sensor 50b and is not directly used to determine a characteristic of the cleaning agents used during the cleaning process.

In still another embodiment, algorithm 200 utilizes information from one or more contact pressure sensors 70 to determine the usability status. Pressure sensors 70 provide information regarding physical aspects of the cleaning process based on the pressure applied to the surfaces of person support apparatus 20 by the cleaning person and/or a tool used by the cleaning person. Pressure sensors 70 are coupled to support deck 30 and/or the cushion (not shown) that forms a support surface for an occupant of person support apparatus 20 and are adapted to detect a pressure applied to support deck 30 and/or the cushion. In this embodiment, initiation of the usability status process at 202 causes controller 58 to monitor the signals from pressure sensors 70. The signals from pressure sensors 70 are utilized in the manner disclosed in commonly assigned U.S. Pat. Publication No. 2016/0148485 filed Nov. 20, 2015, by Hayes et al. and entitled SYSTEM AND METHOD OF MANAGING THE CLEANING OF A MEDICAL APPARATUS, to determine whether the applied pressure during the cleaning process indicates that the physical act of the cleaning process was acceptable. Controller 58 uses the information regarding the physical act of the cleaning process, in addition to information received from sensors 50a-d, to output a signal indicative of the usability status at 210.

In one example, if the data from pressure sensors 70 indicate the physical act of the cleaning process was acceptable and the data from chemical sensors 50a indicates the cleaning process was acceptable, controller 58 outputs a signal at 210 indicating person support apparatus 20 is cleaned and/or ready for use. If the data from pressure sensors 70 indicates the physical act of the cleaning process was unacceptable, even though the data from chemical sensors 50a indicates the cleaning solution was acceptable, controller 58 outputs a signal at 210 indicating that person support apparatus 20 is not cleaned and/or not ready for use. Optionally, controller 58 outputs a signal at 210 indicating that the physical act of the cleaning process was unacceptable and should be repeated. If the data from pressure sensors 70 indicates that the physical act of the cleaning process was acceptable, but the data from chemical sensors 50a indicates that the cleaning solution was not correct, controller 58 outputs a signal at 210 indicating that person support apparatus 20 is not cleaned and/or not ready for use. Optionally, controller 58 outputs a signal at 210 indicating that the chemical solution used in the cleaning process was unacceptable and should be repeated or remade.

Referring now to FIG. 8, another algorithm 400 is depicted for determining a usability status of person support apparatus 20. Algorithm 400 differs from algorithms 100 and 200 in that algorithm 400 utilizes outputs from ambient air pressure sensor 50c. Algorithm 400 is used alone or in combination with any of steps of algorithms 100 and/or 200 described herein. Following initiation of algorithm 400 at step 402, which may be triggered in the same manners discussed above for triggering algorithm 100, air pressure sensor 50c is activated to begin detecting the local air pressure. Air pressure sensor 50c detects the local air pressure at step 404 through a single reading or multiple repeated readings. At step 406 air pressure sensor 50c outputs a signal indicative of the local air pressure to controller 58.

Controller 58 compares the output signal to reference data at step 408 to determine a status of person support apparatus 20 based on the detected pressure. The reference data relates the output signal from air pressure sensor 50c to one or more predetermined statuses of person support apparatus 20. The statuses may correspond to an elevation of person support apparatus 20, such as floor in a building, and/or a pressure-related event, such as being located in a particular area of a healthcare facility wherein negative or positive gauge pressure is maintained for infection control purposes, or for other purposes. In one example, the reference data is in the form of a look-up table identifying output signals, or ranges of output signals, corresponding to predetermined elevations within a building in which person support apparatus 20 is located. In such embodiments, controller 58 uses this comparison to determine a floor on which person support apparatus 20 is currently located within the building. In some instances, the building has one or more designated cleaning areas that are located on one or more specific floors of the building, and this information is stored as part of the reference data. Controller 58 then determines whether or not person support apparatus 20 has been, or is, on a floor in which a cleaning area is located. If not, it does not display an indication that person support apparatus 20 has been cleaned. If so, it displays an indication that person support apparatus 20 has been cleaned if the other criteria discussed above with respect to algorithms 100 and/or 200 are met (e.g. VOC levels are detected above a threshold for a predetermined amount of time).

In some embodiments, controller 58 repeatedly monitors the ambient air pressure readings in order to differentiate fluctuations in pressure based on weather-related changes from those changes in air pressure related to changes in elevation. Changes in elevation due to person support apparatus 20 being moved to a different floor of a building occur rapidly, as compared to air pressure changes due to weather. Controller 58 therefore concludes that person support apparatus 20 has changed elevation by one or more floors if the detected air pressure changes at a rate greater than a stored threshold. Changes in air pressure that occur more slowly than the stored threshold, or a different threshold, are determined to be weather related and are not due to elevation changes. By keeping track of changes in air pressure that occur rapidly due to elevation changes, and by knowing the initial floor on which person support apparatus 20 is located (which may be communicated to controller 58 via user interface 62 or 68), controller 58 is able to continuously determine which floor person support apparatus 20 is located on.

In some situations, the reference data is in the form of a threshold that indicates person support apparatus 20 has been in a particular location and/or gone through a process in which the air pressure changes. The threshold may be in the form of a predetermined change in air pressure over time, a minimum air pressure, or a maximum air pressure. Controller 58 uses this information to determine if person support apparatus 20 has gone through a cleaning process that indicates person support apparatus 20 is ready for use. Alternatively, controller 58 uses this information to determine that person support apparatus 20 was used in a restricted area, such as an infectious disease area, and thus is not ready for use.

Controller 58 outputs a signal indicative of the usability status of person support apparatus 20 at step 410 based on the comparison between the output signal and the reference data at 408. The output signal at step 410 activates an indicator at step 412 that communicates the usability status with a user through user interface 62 and/or remote interface 68. Step 412 may involve the same processes, or be in accomplished in any of the same manners, discussed above with respect to steps 112 and/or 212. Non-limiting examples of indicators activated at step 412 include illuminable status icons, colored lights, and/or a display screen. The indicator may provide information regarding the usability status, the sensed ambient air pressure, the elevation status, and/or pressure-related events.

In another embodiment, algorithm 400 determines that person support apparatus has experienced a predetermined pressure-related event. In one example, the pressure-related event corresponds to entering and/or leaving a designated area. In another example, the pressure-related event corresponds to a cleaning process that involves a change in pressure. For example, an infectious disease control room is typically kept at a negative pressure compared to the surrounding rooms while a clean room is kept at a positive pressure. If the output signal from air pressure sensor 50c indicates a rapid change in air pressure above or below a predetermined threshold, controller 58 outputs a signal at 410 indicating that person support apparatus 20 has entered one of these designated areas.

In one example, if the air pressure signal indicates that person support apparatus 20 has entered an infectious disease control room, control system 54 saves this information for later use in determining the cleaning needs of person support apparatus 20. In one embodiment, this information is used to determine the cleaning protocol for use in cleaning person support apparatus 20 and the reference data for algorithm 200 is set accordingly. For example, the cleaning protocol following use in an infectious disease control room may require a specific cleaning protocol, e.g. predetermined humidity, time, temperature, and pressure, using particular cleaning agents and the reference data for algorithm 200 is set based on the protocol and the particular cleaning agents.

In some healthcare facilities, the cleaning area may be maintained at a particular ambient air pressure. In such situations, person support apparatus 20 can be configured to detect if the air pressure signal indicates that person support apparatus 20 has entered such a cleaning room. If so, controller 58 may generate a signal indicating the presence of person support apparatus 20 in the cleaning area. Alternatively, or additionally, controller 58 is configured to monitor the air pressure over time and compare the monitored air pressure to reference data indicative of a cleaning process within the clean room. For example, a decrease in pressure below a predetermined threshold for a predetermined period of time corresponds to person support apparatus 20 having remained in the cleaning area long enough to be properly cleaned. If the monitored air pressure and the monitored VOC levels (and/or other outputs from sensors 52) satisfy their corresponding thresholds for the requisite periods of time, controller 58 activates an output signal indicating person support apparatus 20 is clean or ready for use. If the monitored air pressure does not satisfy the pressure threshold for a predetermined period of time, or the VOC levels are insufficient, controller 58 activates an output signal indicating person support apparatus 20 is not clean or is not ready for use. Optionally, controller 58 outputs a signal indicating the cleaning process should be repeated. The information regarding usability status based on the air pressure may be stored by control system 54 for later display and/or analysis.

In some embodiments of person support apparatus 20, controller 58 includes training information as part of algorithms 100, 200, or 400. The training information provides feedback to the personnel responsible for cleaning person support apparatus 20. Thus, for example, if a cleaning person begins cleaning person support apparatus 20 but sensor 50 never detects VOC levels above the minimum concentration required, controller 58 may be configured to provide aural or visual feedback to the cleaner indicating to them that not enough cleaning agent has been used. Alternatively, or additionally, if the person support apparatus 20 includes contact pressure sensors 70 that do not detect contact pressure being applied to all of the surfaces that are desirably cleaned, controller 58 may provide aural or visual feedback to the cleaner instructing him or her that one or more surface areas have not been cleaned. Such feedback helps ensure that cleaning standards are maintained uniformly in a healthcare facility, regardless of the different individuals who may carry out the cleaning tasks at different times.

Control system 54 may be configured to use algorithms 100, 200, and 400 in any combination to monitor, track, provide feedback and/or train a user regarding a usability status of a person support apparatus. Algorithms 100, 200, and 400 may be used to provide information regarding usability status of a person support apparatus in real-time and/or information may be saved over time and analyzed. While only a single person support apparatus 20 is illustrated, it will be understood that multiple person support apparatuses 20 will typically be in communication with network server 66, with each person support apparatus 20 providing information regarding its respective usability status to network server 66.

In one embodiment, usability status determined according to algorithms 100, 200, and/or 400 is stored on network server 66 and accessible by a user through remote interface 68 or user interface 62. In one example, the saved usability status information is searchable so that a user may look up information regarding a particular person support apparatus 20. Non-limiting examples of information that may be searched includes information regarding the last time the particular person support apparatus 20 was cleaned, what it was cleaned with, whether it was deemed a hazard for an occupant having a compromised health status, and it's previous location. In one example, a healthcare worker searches this information prior to assigning an occupant to the particular person support apparatus 20.

In another embodiment, the usability status information is analyzed by additional applications to track a variety of information. For example, the usability status information may be saved and analyzed to determine how often each person support apparatus 20 is cleaned or how often each person support apparatus 20 is insufficiently cleaned, not suitable for use, or not safe for use by occupants with a compromised health status. In another example, the usability status information is used to track how often the incorrect cleaning solution or concentration of cleaning solution is used. In still another example, the usability status information is used to track where each person support apparatus 20 travels in the building in which they are located. The types of studies are customizable according to the interests of the healthcare facility and/or third party, or according to the interests of a group of healthcare facilities. Such studies might include, for example: correlations between the usability status and clinical outcomes; housekeeping procedure studies; or infection control studies.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
   a support adapted to support thereon an occupant of the person support apparatus;
   a first sensor configured to detect a volatile organic compound level present in ambient air and generate a first output signal based on the detected volatile organic compound level;
   a second sensor configured to detect an ambient humidity level and to generate a second output signal based on the detected ambient humidity level; and
   a controller configured to receive the first and second output signals from the first and second sensors and determine a cleanliness status of the person support apparatus based upon the volatile organic compound level and the humidity level.

2. The person support apparatus of claim 1 wherein the volatile organic compound level detected by the first sensor includes a volatile organic compound associated with a cleaning agent used to clean the person support apparatus.

3. The person support apparatus of claim 1 wherein the controller is further configured to measure an amount of time during which the first and second output signals are received and to use the measured amount of time to determine the cleanliness status.

4. The person support apparatus of claim 1 further comprising an atmospheric pressure sensor and a temperature sensor.

5. The person support apparatus of claim 4 wherein the controller is further configured to determine the cleanliness status based on output signals from the atmospheric pressure sensor and the temperature sensor.

6. The person support apparatus of claim 1 further comprising:
   a pressure sensor mounted relative to the support, the pressure sensor configured to detect a pressure applied to the support and generate an output signal based on the detected pressure,
   wherein the controller is configured to use the output signal from the pressure sensor to determine the cleanliness status of the person support apparatus.

7. The person support apparatus of claim 1 wherein the controller is adapted to determine the cleanliness status based upon a ratio of the volatile organic compound level and the humidity level.

8. A person support apparatus comprising:
a support adapted to support thereon an occupant of the person support apparatus;
a sensor configured to detect first and second ambient air characteristics and generate first and second output signals based on the detected ambient air characteristics; and
a controller configured to receive the first and second output signals from the sensor and determine a usability status of the person support apparatus based on the output signals; wherein the second ambient air characteristic is a pressure of the air and the controller is adapted to determine a floor of a building on which the person support apparatus is located based upon the pressure of the air.

9. The person support apparatus of claim 8 wherein the usability status indicates whether the person support apparatus is ready for use by the occupant.

10. The person support apparatus of claim 8 wherein the usability status indicates a cleaning status of the person support apparatus.

11. The person support apparatus of claim 10 wherein the cleaning status indicates if the person support apparatus has been cleaned or not cleaned.

12. The person support apparatus of claim 10 wherein the cleaning status indicates if the person support apparatus has been sufficiently cleaned, insufficiently cleaned, or not cleaned.

13. The person support apparatus of claim 8 wherein the usability status indicates whether the person support apparatus is ready for use by the occupant.

14. A person support apparatus comprising:
a support adapted to support thereon an occupant of the person support apparatus;
a first sensor configured to detect a first ambient air characteristic and generate a first output signal based on the detected first characteristic;
a second sensor configured to detect a second ambient air characteristic and generate a second output signal based on the detected second characteristic;
a plurality of pressure sensors adapted to detect pressure applied to the support and generate third output signals based on the detected pressure; and
a controller configured to determine a cleanliness status of the person support apparatus based on both a chemical analysis and a physical analysis, the controller configured to use the first output signal and the second output signal to perform the chemical analysis and to use the third output signals to perform the physical analysis, wherein the physical analysis determines if a physical act of cleaning is acceptable or not.

15. The person support apparatus of claim 14 wherein the first sensor and the second sensor comprise at least one of a volatile organic compound (VOC) sensor, a humidity sensor, an atmospheric pressure sensor, or a temperature sensor.

16. The person support apparatus of claim 14 wherein:
the first sensor comprises a volatile organic compound sensor and the first output signal is indicative of a concentration of volatile organic compounds in the atmosphere adjacent the person support apparatus, and
the second sensor comprises a humidity sensor and the second output signal is indicative of a humidity of the atmosphere adjacent the person support apparatus.

17. The person support apparatus of claim 14 wherein:
the first sensor is configured to detect a first compound, and
the second sensor is configured to detect a second compound.

18. A method of determining a usability status of a person support apparatus, the method comprising:
providing a volatile organic compound sensor configured to detect a concentration of volatile organic compounds in the ambient air adjacent the person support apparatus and generate a first output signal based on the detected concentration;
providing a humidity sensor configured to detect a humidity level in the ambient air adjacent the person support apparatus and to generate a second output signal based on the detected humidity level;
determining the usability status of the person support apparatus based on a combination of the first and second output signals; and
indicating the usability status to a user.

19. The method of claim 18 further comprising providing at least one of an atmospheric pressure sensor and a temperature sensor on the person support apparatus and using an output from the atmospheric pressure sensor or temperature sensor to determine the usability status.

20. The method of claim 18 wherein the usability status indicates:
whether a potential hazard exists for the occupant of the person support apparatus having a compromised health status; or
whether the person support apparatus has been cleaned.

* * * * *